(12) United States Patent
Gumina et al.

(10) Patent No.: US 7,423,025 B2
(45) Date of Patent: Sep. 9, 2008

(54) L-NUCLEOSIDES AS LIGANDS TO ADENOSINE RECEPTORS

(75) Inventors: Giuseppe Gumina, Charleston, SC (US); Craig C. Beeson, Charleston, SC (US); Gary L. Wright, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 11/517,977

(22) Filed: Sep. 8, 2006

(65) Prior Publication Data

US 2007/0054875 A1 Mar. 8, 2007

Related U.S. Application Data

(60) Provisional application No. 60/715,109, filed on Sep. 8, 2005.

(51) Int. Cl.
*A61K 31/70* (2006.01)
*C07H 19/16* (2006.01)

(52) U.S. Cl. ..................... 514/46; 536/27.22

(58) Field of Classification Search .................... None
See application file for complete search history.

(56) References Cited

OTHER PUBLICATIONS

Al Safarjalani et al., "Uptake of nitrobenzylthioinosine and purine β-L-nucleosides by intracellular *Toxoplasma gondii*," *Antimicrob. Agents Chemother.* 2003, 47, 3247-3251.
Angulo et al., "$A_1$ Adenosine receptors accumulate in neurodegenerative structures in Alzheimer's disease and mediate both amyloid precursor protein processing and tau phosphorylation and translocation," *Brain Pathol.* 2003, 13, 440-451.
Baker et al., "Synthetic studies. VIII. Synthesis of 3-amino-3-deoxy-D-ribofuranoside derivatives. A second synthesis of 3-amino-3-deoxy-D-ribose," *J. Am. Chem. Soc.* 1955, 77, 7-12.
Baker et al., "Synthetic studies. IX. Total synthesis," *J. Am. Chem. Soc.* 1955, 77, 12-15.
Behan and Stone, "Enhanced neuronal damage by co-administration of quinolinic acid and free radicals, and protection by adenosine $A_{2a}$ receptor antagonists," *Brit. J. Pharmacol.* 2002, 135, 1435-1442.
Blum et al., "The adenosine $A_1$ receptor agonist adenosine amine congener exerts a neuroprotective effect against the development of striatal lesions and motor impairments in the 3-nitropropionic acid model of neurotoxicitym," *J. Neurosci.* 2002, 22, 9122-9133.
Brown et al., "Evidence for stereospecificity of the P1-purinoceptor," *Br. J. Pharmacol.* 1982, 75, 101-107.
Burnstock et al., "Evidence that the P1-purinoceptor in the guinea-pig *taenia coli* is an A2-subtype," *Br. J. Pharmacol.* 1984, 81, 533-541.
Canyon and Dobson, "Pretreatment with an adenosine A1 receptor agonist and lidocaine: A possible alternative to myocardial ischemic preconditioning," *J. Thorac. Cardiovasc. Surg.* 2005, 130, 371-377.
Carter et al., "Isolation and functional characterization of the PfNT1 nucleoside transporter gene from *Plasmodium falciparum*," *J. Biol. Chem.* 2000, 275, 10683-10691.

Chase et al., "Translating $A_{2a}$ antagonist KW6002 from animal models to parkinsonian patients," *Neurology* 2003, 61, S107-S111.
Chen et al., "Neuroprotection by caffeine and $A_{2A}$ adenosine receptor inactivation in a model of Parkinson's disease," *J. Neurosci.* 2001, 21, 143-148.
Cusack et al., "Effects of D- and L-enantiomers of adenosine, AMP and ADP and their 2-chloro- and 2-azido- analogues on human platelets," *Proc. R. Soc. Lond. B Bio. Sci.* 1979, 206, 139-144.
Cusack and Planker, "Relaxation of isolated *taenia coli* of guinea-pig by enantiomers of 2-azido analogues of adenosine and adenine nucleotides," *Br. J. Pharmacol.* 1979, 67, 153-158.
Dall'Igna et al., "Neuroprotection by caffeine and adenosine $A_{2A}$ receptor blockade of β-amyloid neurotoxicity," *Brit. J. Pharmacol.* 2003, 138, 1207-1209.
Dall'Igna et al., "Caffeine as a neuroprotective adenosine receptor antagonist," *Ann. Pharmacother.* 2004, 38, 717-718.
De Giovanni et al., "Adenosine induced transient cardiac standstill in catheter interventional procedures for congenital heart disease," *Heart* 1998, 80, 330-333.

(Continued)

*Primary Examiner*—Shaojia Anna Jiang
*Assistant Examiner*—L. E. Crane
(74) *Attorney, Agent, or Firm*—Ballard Spahr Andrews & Ingersoll, LLP

(57) ABSTRACT

Disclosed herein are compounds having Formula I, which are non-natural L-adenosine analogs. Also disclosed are their methods of making. Still further, disclosed are the uses of the disclosed compounds to treat cardiovascular disease, ischemia related injuries; and neurodegenerative diseases. The compounds disclosed herein have the formula:

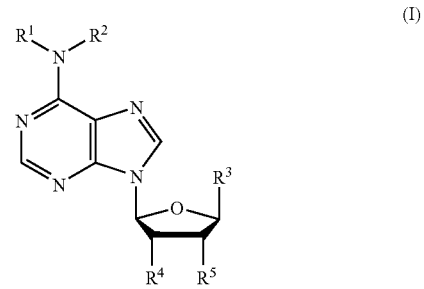

(I)

wherein $R^1$ and $R^2$ are, independently, H, branched or straight-chain, substituted or unsubstituted alkyl, alkenyl, alkynyl, or aryl; $R^3$ is branched or straight-chain, substituted or unsubstituted alkyl, hydroxy-alkyl, or —C(=O)NR$^6$R$^7$; and $R^4$ and $R^5$ are, independently, H, hydroxy, halogen, and NR$^8$R$^9$, wherein $R^6$, $R^7$, $R^8$, and $R^9$ are, independently, H, branched or straight-chain, substituted or unsubstituted alkyl, alkenyl, alkynyl, or aryl.

3 Claims, 7 Drawing Sheets

OTHER PUBLICATIONS de Jong et al., "The role of adenosine in preconditioning," *Pharmacol. Ther*. 2000, 87, 141-149.

de Jonge et al., "Role of adenosine and glycogen in ischemic preconditioning of rat hearts," *Eur. J. Pharmacol*. 2001, 414, 55-62.

DeNinno et al., "3'-Aminoadenosine-5'-uronamides: discovery of the first highly selective agonist at the human adenosine $A_3$ receptor," *J. Med. Chem*. 2003, 46, 353-355.

Donato and Gelpi, "Adenosine and cardioprotection during reperfusion—an overview," *Mol. Cell. Biochem*. 2003, 251, 153-159.

Fishman et al., "The A3 adenosine receptor as a new target for cancer therapy and chemoprotection," *Exp. Cell Res*. 2001, 269, 230-236.

Fishman et al., "A3 adenosine receptor as a target for cancer therapy," *Anticancer Drugs* 2002, 13, 437-443.

Fredholm et al., "International Union of Pharmacology. XXV. Nomenclature and classification of adenosine receptors," *Pharmacol. Rev*. 2001, 53, 527-552.

Gilbert et al., "Synthesis of L,L-puromycin," *Tetrahedron* 2005, 61, 8339-8344.

Glover et al., "Reduction of infarct size and post-ischemic inflammation from ATL-146e, a highly selective adenosine $A_{2a}$ receptor agonist, in reperfused canine myocardium," *Am. J. Physiol. Heart Circ. Physiol*. 2005, 288, H1851-H1858.

Gumina et al., "L-Nucleosides as chemotherapeutic agents," *FEMS Microbiol. Lett*. 2001, 202, 9-15.

Gumina et al., "L-Nucleosides: Antiviral activity and molecular mechanism," *Curr. Top. Med. Chem*. 2002, 2, 1065-1086.

Hafner, "Cytosensor® Microphysiometer: technology and recent applications," *Biosens. Bioelectron*. 2000, 15, 149-158.

Hein et al., "Functional and molecular characterization of receptor subtypes mediating coronary microvascular dilation to adenosine," *J. Mol. Cell. Cardiol*. 2001, 33, 271-282.

Jordan et al., "Adenosine $A_2$ receptor activation attenuates reperfusion injury by inhibiting neutrophils accumulation, superoxide generation, and coronary endothelial adherence," *J. Pharmacol. Exp. Ther*. 1997, 280, 301-309.

Jurovcik et al., "The utilization of L-adenosine by mammalian tissues," *FEBS Lett*. 1971, 18, 274-276.

McConnell et al., "The cytosensor microphysiometer: biological applications of silicon technology," *Science* 1992, 257, 1906-1907.

Müller, "Medicinal chemistry of adenosine $A_3$ receptor ligands," *Curr. Top. Med. Chem*. 2003, 3, 445-462.

Mustafa and Askar, "Evidence suggesting an $R_a$-type adenosine receptor in bovine coronary arteries," *J. Pharmacol. Exp. Ther*. 1985, 232, 49-56.

Nair and Emanuel, "Synthetic design, stereochemistry, and enzymatic activity of a reversed aminoacyl nucleoside: An analogue of puromycin," *J. Am. Chem. Soc*. 1977, 99, 1571-1576.

Nussbaum et al., "Transient cardiac standstill induced by adenosine in the management of intraoperative aneurysmal rupture: Technical case report," *Neurosurgery* 2000, 47, 240-243.

Okada et al., "Two-phase response of acid extrusion triggered by purinoceptor in Chinese hamster ovary cells," *Eur. J. Pharmacol*. 2002, 455, 19-25.

Okamura et al., "Structure-activity relationships of adenosine $A_3$ receptor ligands: new potential therapy for the treatment of glaucoma," *Bioorg. Med. Chem. Lett*. 2004, 14, 3775-3779.

Patel et al., "Comparison of human recombinant adenosine A2B receptor function assessed by Fluo-3-AM fluorometry and microphysiometry," *Br. J. Pharmacol*. 2003, 138, 671-677.

Peart and Headrick, "Adenosine-mediated early preconditioning in mouse: protective signaling and concentration dependent effects," *Cardiovasc. Res*. 2003, 58, 589-601.

Pinna et al., "New adenosine $A_{2A}$ receptor antagonists: actions on Parkinson's disease models," *Eur. J. Pharmacol*. 2005, 512, 157-164.

Rabinowitz et al., "Potentiometric measurement of intracellular redox activity," *J. Am. Chem. Soc*. 1998, 120, 2464-2473.

Schwarzschild et al., "Neuroprotection by caffeine and more specific $A_{2a}$ receptor antagonists in animal models of Parkinson's disease," *Neurology* 2003, 61, S55-S61.

Shryock and Belardinelli, "Adenosine and adenosine receptors in the cardiovascular system: biochemistry, physiology, and pharmacology," *Am. J. Cardiol*. 1997, 79, 2-10.

Sutherland et al., "Mouse isolated perfused heart: characteristics and cautions," *Clin. Exp. Pharmacol. Physiol*. 2003, 30, 867-878.

Sutherland et al., "Responses to ischemia and reperfusion in the mouse isolated perfused heart and the phenomenon of 'contractile cycling'," *Clin. Exp. Pharmacol. Physiol*. 2003, 30, 879-884.

Tikh et al., "Contractile effects of adenosine A1 and A2A receptors in the isolated murine heart," *Am. J. Physiol. Heart Circ. Physiol*. 2005.

Tracey et al., "Selective adenosine $A_3$ receptor stimulation reduces ischemic myocardial injury in the rabbit heart," *Cardiovasc. Res*. 1997, 33, 410-415.

Tracey et al., "Novel $N^6$-substituted adenosine 5'-N-methyluronamides with high selectivity for human adenosine $A_3$ receptors reduce ischemic myocardial injury," *Am. J. Physiol. Heart Circ. Physiol*. 2003, 285, H2780-H2787.

Vu et al., "Piperazine derivatives of [1,2,4]triazolo [1,5-a][1,3,5]triazine as potent and selective adenosine $A_{2a}$ receptor antagonists," *J. Med. Chem*. 2004, 47, 4291-4299.

Vu, et al., "Novel diamino derivatives of [1,2,4]triazolo [1,5-a][1,3,5]triazine as potent and selective adenosine $A_{2a}$ receptor antagonists," *J. Med. Chem*. 2005, 48, 2009-2018.

Wang et al., "Are L-adenosine and its derivatives substrates for S-adenosyl-L-homocysteine hydrolase?" *J. Med. Chem*. 2005, 48, 3649-3653.

Reagents and conditions: (a) seven steps, ref. 18; (b) TBDPSCl, Py, rt, 4h; (c) AcOH, H₂SO₄, rt, overnight, then Ac₂O, Py, rt, 4h; (d) silylated 6-chloropurine, TMSOTf, MeCN, 0°C to rt, overnight; (e) Et₃N·HF, THF, rt, 24h; (f) TEMPO, BAIB, rt, 24h; (g) NaIO₄, RuCl₃·H₂O, H₂O/MeCN/CCl₄, rt, 24h; (h) EtOC(O)Cl, Et₃N, DMF, 0°C, 10min, then 40% MeNH₂/H₂O, 0°C to rt, 48h.

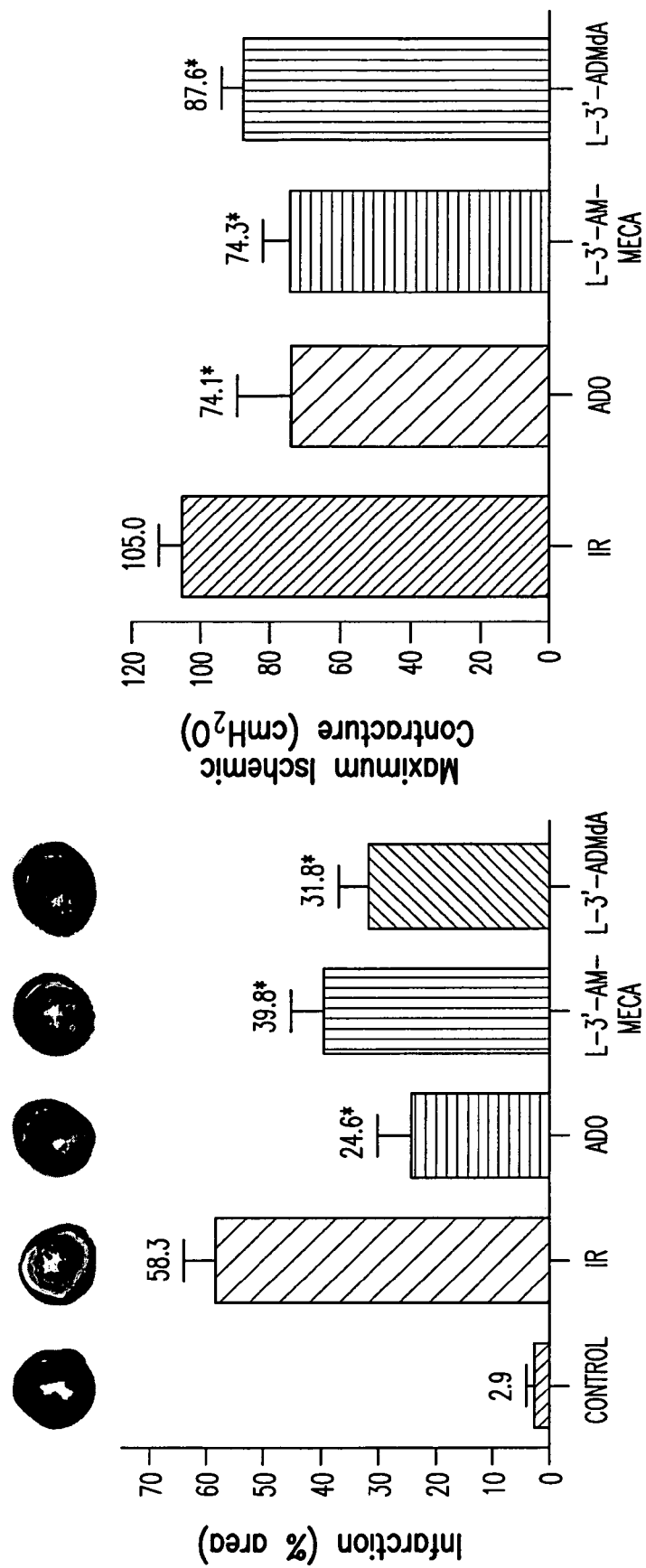

L-NUCLEOSIDES AS LIGANDS TO ADENOSINE RECEPTORS

CROSS REFERENCE TO RELATED APPLICATIONS

This application claims the benefit of priority to U.S. Provisional Application No. 60/715,109, filed on Sep. 8, 2005, which is incorporated by reference herein in its entirety.

BACKGROUND

Adenosine is an important mediator of numerous biological functions both in the nervous system and in peripheral tissues. It exerts its action by interacting with at least four different receptor (AR) subtypes ($A_1$, $A_{2a}$, $A_{2b}$, and $A_3$) (Fredholm, et al., *J. International Union of Pharmacology*. V. Nomenclature and classification of adenosine receptors. *Pharmacol. Rev.* 2001, 53, 527-552). Several studies on the action of adenosine in different tissues showed the potential benefits of ligands (agonists or antagonists) to AR for the treatment of several diseases. Thus, cardioprotective action has been attributed to $A_1AR$,[2] $A_{2a}AR$[3] and $A_3AR^{2b,4,5}$ agonists, whereas $A_1AR$[6] and $A_{2a}AR$[7] antagonists show potential anti-Alzheimer properties. $A_{2a}AR$ antagonists are actively studied as anti-Parkinson agents,[8] and have also been found protective against quinolinic acid and free radical neuronal damage.[9] $A_3$ AR antagonists are under consideration for treatment of glaucoma.[4,10] A selective $A_1AR$ agonist showed neuroprotective effect in a rat model of Huntington's disease.[11] Finally, recent studies indicate that $A_3$ AR maybe targets for cancer therapy and chemoprotection.[12]

Such a range of possible therapeutic applications and the need of fully understand the pharmacological properties of each AR subtype prompted numerous efforts to discover more potent and selective ligands to each receptor subtype. Among many structural modifications reported in literature, L-nucleosides have been rarely considered, probably following early reports of little or no interactions of the L-entantiomers of adenosine, 2-chloroadenosine, 2-azidoadenosine, and N-ethylcarboxamidoadenosine (NECA) with A2 AR in different animal tissues.[13] L-adenosine, a plant hormone, is also inactive on animal enzymes such as S-adenosyl-L-homocysteine hydrolase,[14] and does not interact with mammalian nucleoside transporters.[15] In the past, however, favorable features of L-nucleosides, such as low cellular toxicity[16] and high metabolic stability,[16,17] have been exploited in the design of successful antiviral and promising anticancer agents. The favorable features of L-nucleosides prompted us to evaluate L-3'-amino-3'-deoxy-$N^6$-dimethyladenosine (L-PAN, 1) (FIG. 1), recently synthesized in our laboratory,[18] as an AR agonist. At the same time, in order to evaluate the effect of the favorable 3'-amino and 5'-carboxamide substitutions, we prepared and evaluated the novel analog L-3'-amino-3'-deoxy-$N^6$-methyladenosine-5'-N-methyluronamide (L-3'-AM-MECA, 2), enantiomer of compound 3, a simplified and $A_3AR$-selective analog of the non-selective agonist IB-MECA (FIG. 1).

SUMMARY

In accordance with the purposes of the disclosed materials, compounds, compositions, and methods, as embodied and broadly described herein, the disclosed subject matter, in one aspect, relates to compounds and compositions and methods for preparing and using such compounds and compositions. In a further aspect, the disclosed subject matter relates to L-nucleosides as ligands for adenosine receptors. Methods for making and using the disclosed compounds are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

The accompanying figures, which are incorporated in and constitute a part of this specification, illustrate several aspects described below.

FIG. 3B shows infarction area following ischemia-reperfusion (IR). Heart tissue was stained with TTC, which is reduced to the bright red triphenyl formazane by viable cells. Red areas indicate living tissue, while colorless or pale yellow areas indicate necrotic tissue. Data is expressed as the percentage of area that lacks significant TTC staining. FIG. 3C shows time until onset of contracture.

DETAILED DESCRIPTION

Figure 1:
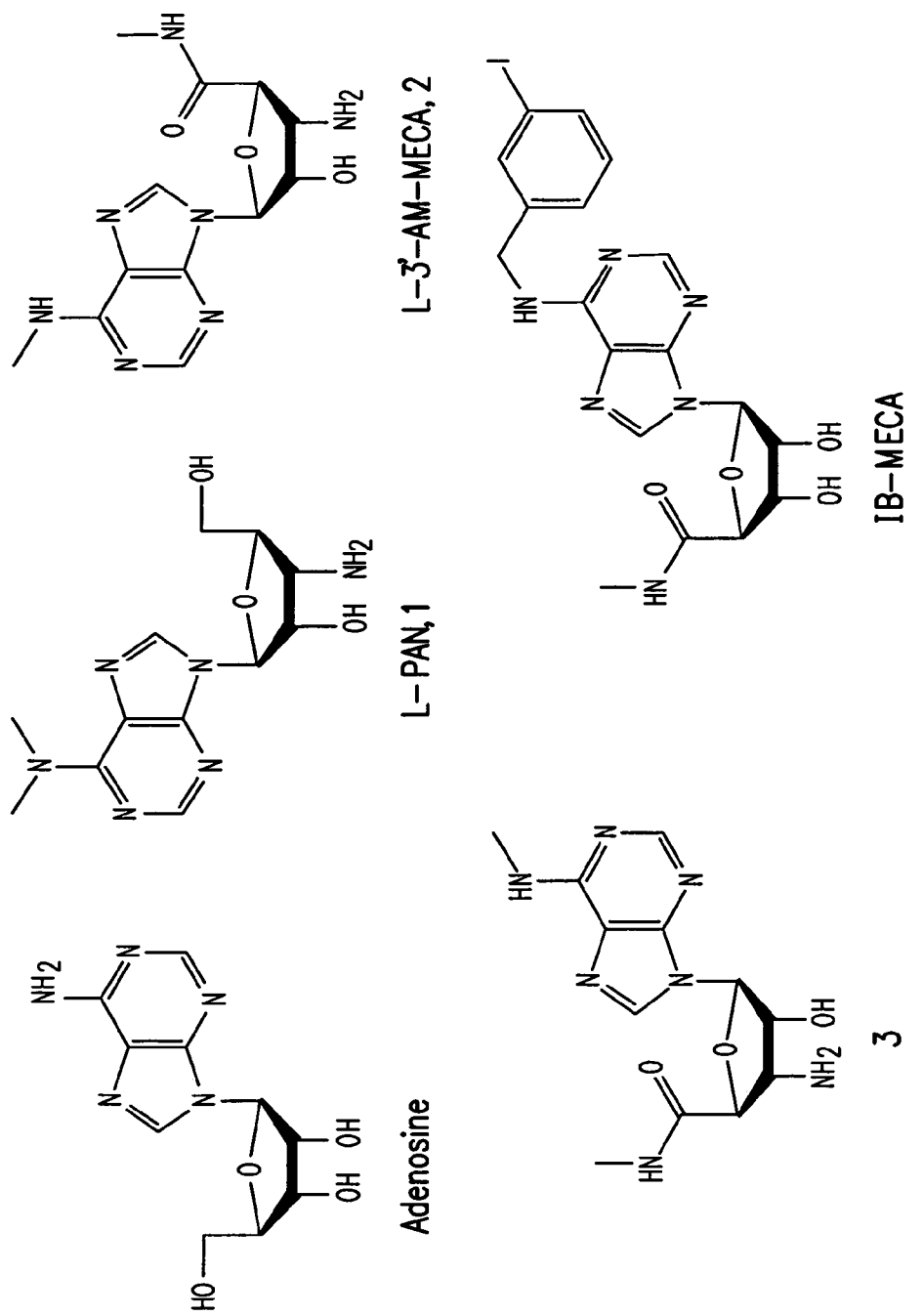
FIG. 1 shows the structures of adenosine, L-PAN (1), L-3'-AM-MECA (2), the selective $A_3AR$ agonist (3), and IB-MECA.

The materials, compounds, compositions, and methods described herein may be understood more readily by reference to the following detailed description of specific aspects of the disclosed subject matter and the Examples included therein and to the Figures.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such component, and the like.

"Optional" or "optionally" means that the subsequently described event or circumstance can or cannot occur, and that the description includes instances where the event or circumstance occurs and instances where it does not. For example, the phrase "L is an optional linker" means that L may or may not be present in the composite and that the description includes both composites where L is present (e.g., linking a first active substance to a second active substance) and composites where L is not present, in which case the first and second active substances are directly bonded together.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

Chemical Definitions

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

The term "independently selected" is used herein to indicate that the R groups, e.g., $R^1$, $R^2$, $R^3$ or $R^4$, can be identical or different (e.g., $R^1$, $R^2$ and $R^3$ can all be substituted alkyls, or $R^1$ and $R^4$ can be a substituted alkyl and $R^3$ can be an aryl, etc.). Moreover, "independently selected" means that in a multiplicity of R groups with the same name, each group can be identical to or different from each other (e.g., one $R^1$ can be an alkyl, while another $R^1$ group in the same compound can be aryl; one $R^2$ group can be H, while another $R^2$ group in the same compound can be alkyl, etc.).

A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

As used herein, the term "alkyl" means $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tent-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

The alkyl group can be optionally substituted (i.e., a "substituted alkyl") with one or more alkyl group substituents which can be the same or different, where "alkyl group substituent" includes but is not limited to alkyl, substituted alkyl, halo, arylamino, acyl, hydroxy, aryl, aryloxy, alkoxyl, alkylthio, arylthio, aralkyloxy, aralkylthio, carboxy, alkoxycarbonyl, oxo and cycloalkyl. Suitable substituted alkyls include, for example, benzyl, trifluoromethyl and the like. There can be optionally inserted along the alkyl chain one or more oxygen, sulfur or substituted or unsubstituted nitrogen atoms, wherein the nitrogen substituent is hydrogen, alkyl (also referred to herein as "alkylaminoalkyl"), or aryl. Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, hydroxy, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group, Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl. "Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_r$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

The term "aryl" is used herein to refer to an aromatic substituent which can be a single aromatic ring or multiple aromatic rings which are fused together, linked covalently, or linked to a common group such as a methylene or ethylene moiety. The common linking group can also be a carbonyl as in benzophenone or oxygen as in diphenylether or nitrogen in diphenylamine. The term "aryl" specifically encompasses heterocyclic aromatic compounds. The aromatic ring(s) can include phenyl, naphthyl, biphenyl, diphenylether, diphenylamine and benzophenone among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

Specific examples of aryl groups include but are not limited to cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The aryl group can be optionally substituted (i.e., a "substituted aryl") with one or more aryl group substituents which can be the same or different, where "aryl group substituent" includes alkyl, substituted alkyl, aryl, substituted aryl, aralkyl, hydroxy, alkoxyl, aryloxy, aralkoxyl, carboxy, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene and —NR'R", where R' and R" can be each independently hydrogen, alkyl, substituted alkyl, aryl, substituted aryl, and aralkyl. Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aylalkyl" refers to the group -aryl-alkyl. The aryl group can be phenyl or napthyl or can be heteroaryl. The alkyl can be cyclic or branched or further substituted, for example, by a halo, hydroxy, or nitro group. Exemplary arylalkyl compounds include, but are not limited to 4-tent-butylphenyl, 3-methylphenyl, 2-isopropylphenyl, 2,6-di-isopropylphenyl, 2,6-dimethylphenyl, 3,5-di-tent-butylphenyl, and 2,4,6-trimethylphenyl.

The term "alkenyl" is used to denote a branched or straight-chain hydrocarbon group having a carbon-carbon double bond. Representative alkenyl groups include, but are not limited to, ethenyl, propenyl, butenyl, pentenyl, hexenyl, octenyl, and butadienyl. The carbon atoms of the double bond can be further substituted by substituents that can be the same or different and can include hydrogen, alkyl, substituted alkyl, aryl, hydroxyalkyl, aralkyl, arylalkyl, halo, arylamino, alkylamino, acyl, alkylthio, arylthio, cycloalkyl, carboxy, alkyloxycarbonyl, aryloxycarbonyl, alkylcarbamoyl, carbamoyl, dialkylcarbamoyl, and the like.

The term "alkynyl" is used to denote a branched or straight-chain hydrocarbon group having a carbon-carbon triple bond. Representative alkynyl groups include, but are not limited to, ethynyl, propynyl, butynyl, pentynyl, hexynyl, and heptynyl groups, and the like.

A structure represented generally by a formula such as:

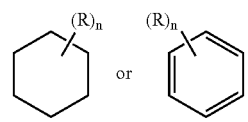

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an avail able carbon of the ring structure rather than on another R group. For example, the structure:

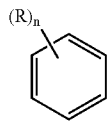

wherein n is an integer from 0 to 2 comprises compound groups including, but not limited to:

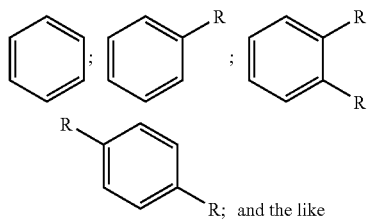

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

The term "alkoxy" is used herein to refer to the —$OZ^1$ radical, where $Z^1$ is selected from the group consisting of alkyl, substituted alkyl, cycloalkyl, substituted cycloalkyl, heterocycloalkyl, substituted heterocycloalkyl, silyl groups and combinations thereof as described herein. Suitable alkoxy radicals include, for example, methoxy, ethoxy, benzyloxy, t-butoxy, and the like. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

The term "amino" is used herein to refer to the group —$NZ^1Z^2$, where each of $Z^1$ and $Z^2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof. Additionally, the amino group can be represented as $N^+Z^1Z^2Z^3$, with the previous definitions applying and $Z^3$ being either H or alkyl.

"Aralkyl" refers to an aryl-alkyl- group wherein aryl and alkyl are as previously described, and included substituted aryl and substituted alkyl. Exemplary aralkyl groups include benzyl, phenyiethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroylis as previously described.

The term "carbonyl" refers to the —(C=O)— group.

The term "carboxyl" refers to the —COOH group.

The terms "halo," "halide," or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

A "heteroatom," as used herein, is an atom other than carbon. In some embodiments, the heteroatoms are selected from the group consisting of N, O, P, S, Si, B, Ge, Sn, and Se. In some embodiments of the presently disclosed subject matter, the heteroatoms are selected from one of N and O.

The term "reflux" and grammatical derivations thereof refer to boiling a liquid, such as a solvent, in a container, such as a reaction flask, with which a condenser is associated, thereby facilitating continuous boiling without loss of liquid, due to the condensation of vapors on the interior walls of the condenser.

The term "aprotic solvent" refers to a solvent molecule which can neither accept nor donate a proton. Typical aprotic solvents include, but are not limited to, acetone, acetonitrile, benzene, butanone, butyronitrile, carbon tetrachloride, chlorobenzene, chloroform, 1,2-dichloroethane, dichloromethane, diethyl ether, dimethylacetamide, N,N-dimethylformamide (DMF), dimethylsulfoxide (DMSO), 1,4-dioxane, ethyl acetate, ethylene glycol dimethyl ether, hexane, N-methylpyrrolidone, pyridine, tetrahydrofuran (THF), and toluene. Certain aprotic solvents are polar solvents. Examples of polar aprotic solvents include, but are not limited to, acetone, acetonitrile, butanone, N,N-dimethylformamide, and dimethylsulfoxide. Certain aprotic solvents are non-polar solvents. Examples of nonpolar, aprotic solvents include, but are not limited to, diethyl ether, aliphatic hydrocarbons, such as hexane, aromatic hydrocarbons, such as benzene and toluene, and symmetrical halogenated hydrocarbons, such as carbon tetrachloride.

The term "protic solvent" refers to a solvent molecule which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

Materials and Compositions

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Also, disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a composition is disclosed and a number of modifications that can be made to a number of components of the composition are discussed, each and every combination and permutation that are possible are specifically contemplated unless specifically indicated to the contrary. Thus, if a class of components A, B, and C are disclosed as well as a class of components D, E, and F and an example of a composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

The presently disclosed subject matter in some embodiments describes non-natural analogs of the natural nucleoside adenosine. The presently disclosed analogs of adenosine include, but are not limited to, compounds of Formula (I):

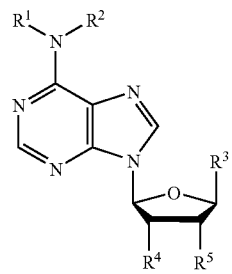

wherein $R^1$ and $R^2$ are independently selected from the group consisting of H, branched or straight-chain alkyl, substituted branched or straight-chain alkyl, branched or straight-chain alkenyl, substituted branched or straight-chain alkenyl, branched or straight-chain alkynyl, substituted branched or straight-chain alkynyl, aryl and substituted aryl; $R^3$ is selected from the group consisting of branched or straight-chain alkyl, branched or straight-chain substituted alkyl, including branched or straight-chain alkyl alcohols, and C(=O)$NR^6R^7$, wherein $R^6$ and $R^7$ are independently selected from the group consisting of H, branched or straight-chain alkyl, substituted branched or straight-chain alkyl, branched or straight-chain alkenyl, substituted branched or straight-chain alkenyl, branched or straight-chain alkynyl, substituted branched or straight-chain alkynyl, aryl, and substituted aryl; and $R^4$ and $R^5$ are independently selected from the group consisting of H, hydroxy, halogen, and $NR^8R^9$, wherein $R^8$ and $R^9$ are independently selected from the group consisting of H, branched or straight-chain alkyl, substituted branched or straight-chain alkyl, branched or straight-chain alkenyl, substituted branched or straight-chaih alkenyl, branched or straight-chain alkynyl, substituted branched or straight-chain alkynyl, aryl, and substituted aryl.

In some embodiments, $R^1$ is methyl, $R^2$ is H, $R^3$ is C(=O)$NHCH^3$, $R^4$ is OH, and $R^5$ is $NH^2$. In some embodiments, $R^1$ and $R^2$ are each methyl, $R^3$ and $R^4$ are each hydroxy, and $R^5$ is $NH^2$.

Adenosine exerts its biological function by acting on specific receptors in the body. This interaction produces a number of responses associated with, for example, a response to cellular stress. Compounds that interact with adenosine receptors have many potential applications as, including, but not limited to, cardioprotective agents, neuroprotective agents, anti-Alzheimer agents, anti-Parkinson agents, anti-hypertensive agents, anti-glaucoma agents, and the like.

The presently disclosed compounds in some embodiments are non-natural L-enantiomers of modified purine nucleosides. L-nucleosides have shown activity as antiviral agents and as anticancer agents by virtue of their ability to interact with human kinases and inhibit viral or human nucleic acid polymerases. The presently disclosed compounds are the first examples of L-nucleosides acting on biological systems other than kinases or polymerases. This characteristic of the presently disclosed compounds can be applicable to opening new research areas in pharmacology and drug discovery. When used as a drug or therapeutic agent, for example, in the treatment of cardiovascular diseases, Alzheimer's disease, and Parkinson's disease, the presently disclosed compounds are likely to enjoy the benefits derived from its nature of being an L-nucleoside, such as low cellular toxicity and long-lasting activity.

More particularly, the presently disclosed L-adenosine analogs, in some embodiments, are agonists to the adenosine receptors. For example, in an ischemia/reperfusion model on Langendorff perfused mouse heart, the presently disclosed L-adenosine analogs, in some embodiments, exhibit cardioprotective action as measured by decreased infarction area and decreased maximum ischemic contracture. Further, the ability of the presently disclosed L-adenosine analogs to increase the azide-induced Pasteur in L6 myoblasts was measured by microphysiometer. In some embodiments, the presently disclosed L-adenosine analogs exhibit a greater increase in the Pasteur effect than that observed for adenosine and known agonists. Without wishing to be bound to any one particular theory, it is believed that because adenosine receptors are involved in the Pasteur effect, this effect, along with the cardioprotection described hereinabove, supports an agonistic effect on adenosine receptors.

In summary, the presently disclosed subject matter provides the first L-nucleosides acting as agonists to adenosine receptor. Because the activity of known anti-viral and anti-tumor L-nucleosides is believed to be due to the metabolic activation to their triphosphate via interaction with nucleoside kinases, the presently disclosed compounds are the only known examples of L-nucleosides that interact with animal enzymes different than kinases. Thus, the presently disclosed subject matter provides a new avenue for the search for adenosine receptor ligands.

Pharmaceutical Compositions

Any of the compositions disclosed herein can be used therapeutically in combination with a pharmaceutically acceptable carrier. In another aspect, any of the compositions disclosed herein can be used prophylactically, i.e., as a preventative agent, with a pharmaceutically acceptable carrier. The compositions disclosed herein can be conveniently formulated into pharmaceutical compositions composed of one or more of the compositions disclosed herein in association with a pharmaceutically acceptable carrier. See, e.g., *Remington's Pharmaceutical Sciences*, latest edition, by E. W. Martin Mack Pub. Co., Easton, Pa., which discloses typical carriers and conventional methods of preparing pharmaceutical compositions that can be used in conjunction with the preparation of formulations of the compositions disclosed herein and which is incorporated by reference herein. Such pharmaceutical carriers, most typically, would be standard carriers for administration of compositions to humans and non-humans, including solutions such as sterile water, saline, and buffered solutions at physiological pH. Other compounds will be administered according to standard procedures used by those skilled in the art.

Depending on the intended mode of administration, the pharmaceutical compositions can be in the form of, for example, solids, semi-solids, liquids, solutions, suspensions (e.g., incorporated into microparticles, liposomes, etc.), emulsions, gels, or the like, preferably in unit dosage form suitable for single administration of a precise dosage. The pharmaceutical compositions can include, as noted above, an effective amount of the conjugate in combination with a pharmaceutically acceptable carrier and, in addition, can include other carriers, adjuvants, diluents, thickeners, buffers, preservatives, surfactants, etc. Pharmaceutical compositions can also include one or more active ingredients such as other medicinal agents, pharmaceutical agents, antimicrobial agents, anti-inflammatory agents, anesthetics, and the like.

Liquid pharmaceutically administrable compositions can, for example, be prepared by dissolving, dispersing, etc., a composition as described herein and optional pharmaceutical adjuvants in an excipient, such as, for example, water, saline aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see Remington's Pharmaceutical Sciences, referenced above.

The compounds and pharmaceutical compositions described herein can be administered to the subject in a number of ways depending on whether local or systemic treatment is desired, and on the area to be treated. Thus, for example, a compound or pharmaceutical composition described herein can be administered as perfusion buffer. Moreover, a compound or pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein for its teaching of sustained release systems.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives, such as antimicrobials, anti-oxidants, chelating agents, and inert gases and the like, can also be present.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

In one specific aspect, a composition that can increase the concentration of an intracellular metabolite of the HBP is in the form of a solution in Ringer's lactate. For example, the composition can comprise a solution of from about 0.1 mM to about 1 M glucosamine in from about 100% to about 50% Ringer's lactate. In one aspect, the composition can comprise a from about 0.1 mM to about 10 mM, from about 1 mM to about 100 mM, or from 10 mM to 1000 mM (1M) solution in Ringer's lactate. In another aspect, the composition can be in from about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, or 50% Ringer's lactate.

The compositions disclosed herein can be administered to a subject continuously over a period of time, in distinct doses over a period of time, or in one dose. The administration regimen can be chosen by one of skill in the art depending on such factors as depending on the species, age, weight, sex, general condition, the particular composition being administered, and extent of the disease or stress in the subject.

In one aspect, the compositions disclosed herein can be administered to a subject in one dose. In another aspect, the compositions disclosed herein can be administered at from about 5 minutes to about 1 hour, from about 10 minutes to about 50 minutes, or from about 20 minutes to about 40 minutes. In yet another aspect, the compositions disclosed herein can be administered for not more than about 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 minute, where any of the stated values can form an upper or lower endpoint as appropriate.

The disclosed compounds can be used to treat cardiovascular disease and injuries related to ischemia, which can have profound implications in at least four clinical settings: (1) injuries resulting in hemorrhage and hypovolemic shock; (2) recovery from myocardial infarction or stroke; (3) interventional cardiology procedures such as cardiac bypass, fibrinolytic therapy, and angioplasty/stent placement; and (4) preservation of organs prior to and following transplant.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in °C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

All the reactions were carried out under a positive pressure of argon and monitored by TLC on Uniplates (silica gel) purchased from Analtech Co. All the reagents and anhydrous solvents were purchased from commercial sources and used without further purification except where noted. Chromatographic purifications were performed on flash silica gel (particle size 40-63 µm) purchased from Silicycle or TLC grade silica gel (particle size 5-15 µm) purchased from Sorbent Technologies. All solvents for chromatographic purifications were HPLC grade. Melting points were determined on a Barnstead Mel-Temp and are uncorrected. $^1$H NMR spectra were recorded on Varian 400 MHz spectrometer using Me$_4$Si as an internal standard and signals are represented as s (singlet), d (doublet), t (triplet), m (multiplet), or combinations of the above. UV spectra were obtained on a BECKMAN DU-650 spectrophotometer. Optical rotations were measured on a Rudolph Research Analytical Autopol IV digital polarimeter. Elemental analyses were performed by Atlantic Microlabs Inc. Norcross, Ga.

Example 1

Synthesis of L-PAN (1) and L-3'-AM-MECA (2)

Figure 2:
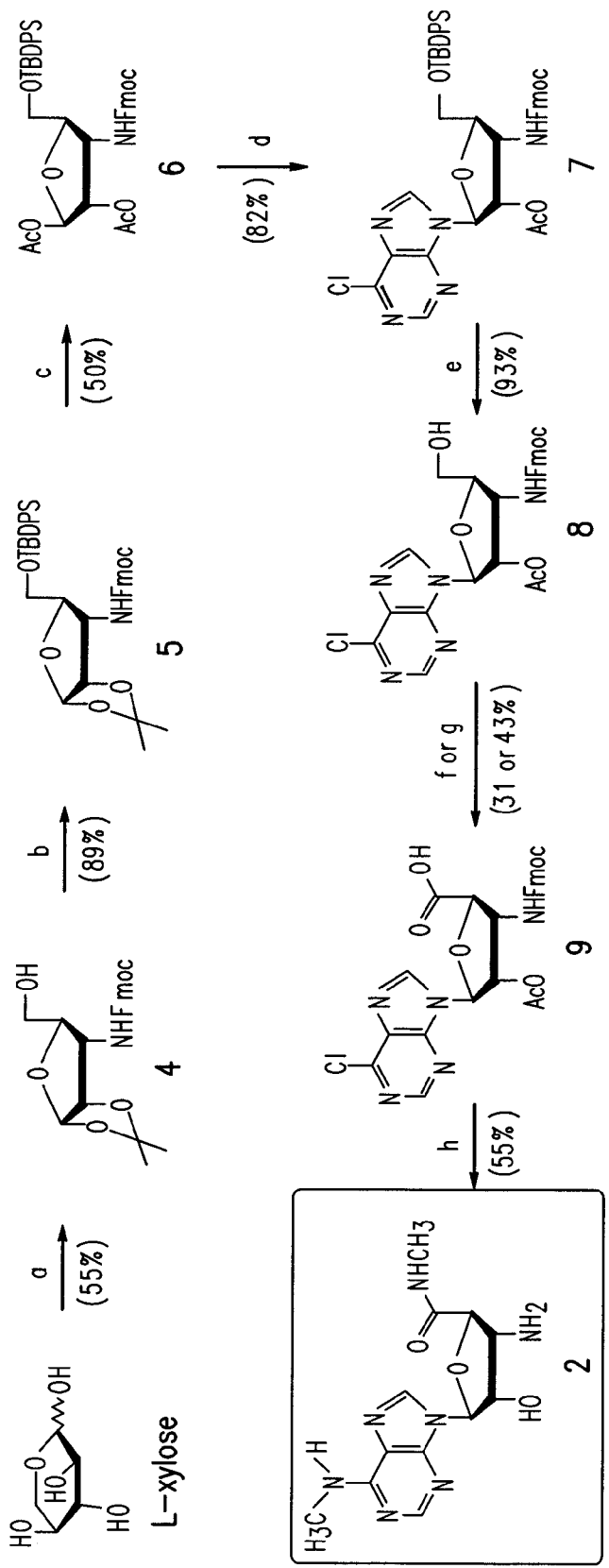
FIG. 2 is a schematic of the synthesis of L-3'-AM-MECA (2).

L-3'-PAN (1) was synthesized from L-xylose in 11 steps as previously reported (Gilbert et al., Synthesis of L,L-puromycin. *Tetrahedron* 61:8339-8344, 2005). L-3'-AM-MECA (2) was prepared from the compound 5 (Scheme 1 of Gilbert et al.; compound 4 in FIG. 2) by the procedure outlined in FIG. 2. Compound 5 was prepared in seven steps from L-xylose as previously described (Scheme 1 of Gilbert et al.).

Thus, protected L-3-amino-3-deoxyribose (4) was protected as the tert-butyldiphenylsilyl ether (5), which was subject to acetolysis to give acetate (6), almost exclusively as the β-anomer, as expected on the basis of the participation of the 2-acetate and supported by the lack of coupling between H-1 and H-2 in the $^1$H NMR spectrum. The $^1$H NMR of the crude reaction mixture showed other minor signals in the anomeric region, but none was of significant intensity to attempt purification or spectroscopic characterization. Acetate (6) was coupled to 6-chloropurine in Vorbrüggen conditions to give protected nucleoside (7). Also in this case, $^1$H NMR of the crude reaction mixture showed only one isomer. The expected β-stereochemistry could be easily confirmed by desilylation of (7) to (8) and conversion of the latter to (1) according to our reported procedure. Oxidation of the primary alcohol functionality of (8) was attempted using two methods. Using (diacetoxyiodo)benzene as the oxidizer and TEMPO as initiator we were able to obtain carboxylic acid (9) in moderate yield. The ruthenium-mediated method afforded lower yields and a product contaminated with a dark impurity, presumably from the catalyst, that could not be purified chromatographically. Conversion of (9) to the mixed anhydride with ethyl hydrogen carbonate and in situ treatment with 40% aqueous methylamine afforded the synthesis of the desired amide (2). The conversion of (9) to (2) is the result of four different reactions: amide formation, Fmoc deprotection, hydrolysis of the 2'-O-acetate and replacement of the 6-chloride. Similarly to what we observed during the synthesis of (1), we noticed that these reactions proceed at different rates, i.e., Fmoc deprotection and amide formation are very fast and complete within a few minutes, whereas acetate hydrolysis usually require 2-4 hours and 6-substitution is the slowest process, requiring several hours to complete. These observations are supported by qualitative TLC and UV data, consistent with the intermediate formation of the 6-chloropurine analog of (2).

5-O-tert-Butylidiphenylsilyl-3-deoxy-3-fluorenylmethylcarbonylamino-1,2-O-(1-methylethylidene)-α-L-ribofuranose (5)

tert-Butyldiphenylchlorosilane (2.4 mL, 9.38 mmol) was added to an ice-cold solution of 4 (2.61 g, 6.34 mmol) and anhydrous pyridine (0.80 mL, 9.89 mmol) in anhydrous dichloromethane (50 mL), and the resulting solution was allowed to warm up to rt and stirred for 24 h. Since the reaction did not proceed to completion, more tert-butyldiphenylsilyl chloride (2.4 mL, 9.38 mmol) and pyridine (0.80 mL, 9.89 mmol) were added, and stirring was continued at rt for 24 h more. The resulting solution was washed with a 0.1 N solution of TLC-grade silica gel was added to the resulting mixture, and solvent was evaporated under reduced pressure, then in vacuo, to a residue that was loaded on a tlc-grade silica gel column packed with 1:4% ethyl acetate/hexanes. Elution with the same solvent gave 5 as a white solid (10.90 g, 82%). Continuing elution with 1:1 ethyl acetate/hexanes allowed recovering unreacted 4 (0.20 g, 2%). 5: $R_f$ 0.16 (1:4 ethyl acetate/hexanes); mp 61-63° C.; $[\alpha]_D^{25}$ -36.94 (c 0.32, $CHCl_3$); $^1H$ NMR ($CDCl_3$, 400 MHz) δ 7.80-7.76 (m, 2H), 7.71-7.69 (m, 4H), 7.63-7.57 (m, 2H), 7.42-7.30 (m, 10H), 5.86 (d, J=2.9 Hz, 1H), 5.08 (d, J=9.6 Hz, 1H), 4.65-4.63 (m, 1H), 4.41 (d, J=6.8 Hz, 2H), 4.34-4.28 (m, 1H), 4.22 (t, J=6.6 Hz, 1H), 3.92-3.88 (m, 1H), 3.87-3.83 (m, 1H), 3.79-3.73 (m, 1H), 2.18 (s, 3H), 2.05 (s, 3H), 1.04 (s, 9H); $^{13}C$ NMR ($CDCl_3$, 100 MHz) δ 155.7, 143.8, 143.7, 141.2, 135.6, 133.2, 133.1, 129.6, 127.7, 127.6, 127.0, 125.0, 119.9, 112.3, 104.2, 80.3, 78.9, 66.9, 62.4, 53.3, 47.1, 26.7, 26.5, 26.3, 19.1; Mass ([M+Na]$^+$) 672. Anal. Calcd for $C_{39}H_{43}NO_6Si$: C, 72.08; H, 6.67; N, 2.16. Found: C, 71.80; H, 6.79; N, 2.10.

5-O-tert-Butyldiphenylsilyl-3-deoxy-1,2-diacetyl-3-fluorenylmethylcarbonylamino-β-L-ribofuranose (6)

Sulfuric acid (60 μL, 1.13 mmol) was added to a stirring mixture of 5 (3.65 g, 5.62 mmol) in acetic acid (50 mL), and the reaction was stirred at rt overnight. Acetic anhydride (7.2 mL, 76.17 mmol) was then added, followed by pyridine (1.7 mL, 21.02 mmol), and the mixture was stirred at rt for 4 h. Volatiles were evaporated in vacuo, and the residue was dissolved in dichloromethane (100 mL), washed with a saturated solution of sodium bicarbonate (20 mL), water (20 mL) and brine (20 mL). The organic solution was dried over magnesium sulfate, filtered and concentrated under reduced pressure to a crude that was purified by tlc-grade silica gel flash chromatography to give 6 as a white solid (1.94 g, 50%). $R_f$ 0.46 (3:7 ethyl acetate/hexanes); mp 70-72° C.; $[\alpha]_D^{26}$ -24.43 (c 1.00, $CHCl_3$); $^1H$ NMR ($CDCl_3$, 400 MHz) δ 7.79-7.76 (m, 2H), 7.68-7.66 (m, 4H), 7.59-7.55 (m, 2H), 7.44-7.28 (m, 10H), 6.12 (s, 1H), 5.17-5.15 (m, 1H), 4.81-4.79 (m, 1H), 4.55-4.42 (m, 3H), 4.22 (t, J=6.6 Hz, 1H), 4.00-3.97 (m, 1H), 3.86 (dd, J=11.3, 3.0, 1H), 3.71 (dd, J=11.3, 4.1, 1H), 2.14 (s, 3H), 1.90 (s, 3H), 1.09 (s, 9H); $^{13}C$ NMR ($CDCL_3$, 100 MHz) δ 170.5, 169.5, 155.5, 143.7, 143.6, 141.3, 135.6, 135.5, 135.2, 130.0, 127.7, 127.7, 127.0, 124.8, 120.0, 97.7, 83.1, 75.7, 66.9, 63.3, 50.7, 47.1, 26.8, 22.9, 20.7, 19.0; Mass ([M+Na]$^+$) 716, ([2M+Na]$^+$) 1409. Anal. Calcd for $C_{40}H_{43}NO_8Si$: C, 69.24; H, 6.25; N, 2.13. Found: C, 69.00; H, 6.24; N, 2.05.

9-(2-O-Acetyl-5-O-tert-butyldiphenylsilyl-3-deoxy-3-fluorenylmethylcarbonylamino-β-L-ribofuranosyl)-6-chloropurine (7)

A mixture of 6-chloropurine (0.67 g, 4.33 mmol) and ammonium sulfate (30 mg, 0.23 mmol) in 1,1,1,3,3,3-hexamethyldisilazane (30 mL) was refluxed for 3 h, then the solvent was removed in vacuo at 35-40° C. A solution of 6 (1.88 g, 2.71 mmol) in anhydrous acetonitrile (30 mL) was added to the residual solid. The resulting solution was cooled to 0° C. and trimethylsilyl triflate (0.78 mL, 4.31 mmol) was added, and the reaction was stirred at rt overnight. The resulting solution was diluted to 100 mL with dichloromethane and slowly added to an ice-cold saturated solution of sodium bicarbonate (200 mL). The organic layer was separated and the aqueous phase was extracted with dichloromethane (2×100 mL). The combined organic extracts were washed with water (50 mL), brine (50 mL), dried over magnesium sulfate, filtered and concentrated to a crude that was purified by tlc-grade silica gel flash chromatography (1:49 methanol/dichloromethane) to give 7 as a white solid (1.75 g, 82%). $R_f$ 0.14 (1:49 methanol/dichloromethane); mp 91-93° C. (dec.); $[\alpha]_D^{25}$ -17.83 (c 0.42, $CHCl_3$); UV (MeOH) $\lambda_{max}$ 264.0, 299.0; $^1H$ NMR ($CDCl_3$, 400 MHz) δ 8.70 (s, 1H), 8.34 (s, 1H), 7.81-7.78 (m, 2H), 7.68-7.57 (m, 6H), 7.44-7.36 (m, 4H), 7.35-7.29 (m, 4H), 7.26-7.22 (m, 2H), 6.15 (s, 1H), 5.67-5.64 (m, 1H), 5.12-5.06 (m, 1H), 4.99-4.95 (m, 1H), 4.55-4.45 (m, 2H), 4.25-4.21 (m, 1H), 4.16-4.12 (m, 1H), 4.03-3.99 (m, 1H), 3.88-3.83 (m, 1H), 2.15 (s, 3H), 1.03 (s, 9H); $^{13}C$ NMR ($CDCl_3$, 100 MHz) δ 169.4, 152.0, 151.1, 150.8, 143.8, 143.5, 143.4, 141.2, 135.5, 135.3, 132.5, 132.2, 132.0, 129.7, 127.6, 127.5, 126.9, 124.7, 124.6, 119.9, 88.0, 83.2, 75.4, 66.8, 62.8, 50.9, 47.0, 26.6, 20.5, 19.0; Mass ([M+H]$^+$) 788, ([M+Na]$^+$) 810, ([2M+Na]$^+$) 1597. Anal. Calcd for $C_{43}H_{42}ClN_5O_6Si$: C, 65.51; H, 5.37; N, 8.88. Found: C, 65.24; H, 5.54; N, 8.56.

9-(2-O-Acetyl-3-deoxy-3-fluorenylmethylcarbonylamino-β-L-ribofuranosyl)-6-chloropurine (8)

Triethylamine trihydrofluoride (1.6 mL, 9.82 mmol) was added to a stirring solution of 7 (1.54 g, 1.95 mmol) in anhydrous tetrahydrofuran (20 mL) at rt, and the resulting solution was stirred at rt for 24 h, then tlc-grade silica gel was added and volatiles were removed under reduced pressure. The residue was loaded on a tlc-grade silica gel column packed with dichloromethane and eluted with a gradient of dichloromethane to 1:19 methanol/dichloromethane to give 8 as a white solid, containing minor impurities (1.00 g, 93%). A small sample was purified by preparative silica gel tlc (1:19 methanol/dichloromethane) to give pure 8 as a white solid. $R_f$ 0.16 (1:19 methanol/dichloromethane); mp 196-197° C.; $[\alpha]^{D22}$ +35.78 (c 0.34, $CHCl_3$); UV (MeOH) $\lambda_{max}$ 264.0, 299.5, 288.5; $^1H$ NMR ($CDCl_3$, 400 MHz) δ 8.77 (s, 1H), 8.42 (s, 1H), 7.79-7.75 (m, 2H), 7.59-7.57 (m, 2H), 7.44-7.38 (m, 2H), 7.35-7.29 (m, 2H), 6.22 (d, J=2.2 Hz, 1H), 5.54-5.52 (m, 1H), 5.20 (d, J=8.0 Hz, 1H), 4.87-4.82 (m, 1H), 4.60-4.49 (m, 2H), 4.29-4.19 (m, 3H), 4.00 (d, J=12.0 Hz, 1H), 3.76 (d, J=12.0 Hz, 1H), 2.11 (s, 3H); $^{13}C$ NMR ($CDCl_3$, 100 MHz) δ 169.5, 156.1, 151.8, 151.3, 150.5, 144.5, 143.4, 141.2, 132.2, 127.7, 126.9, 124.6, 119.9, 88.7, 84.3, 75.5, 66.7, 61.1, 50.5, 47.0, 20.5; Mass ([M+H]$^+$) 550, ([M+Na]$^+$) 572. Anal. Calcd for $C_{27}H_{24}ClN_5O_6$: C, 58.97; H, 4.40; N, 12.73. Found: C, 59.05; H, 4.62; N, 12.33.

1-(6-Chloro-9H-purin-9-yl)-2-O-acetyl-1,3-dideoxy-3-fluorenylmethylcarbonylamino-β-L-ribofuranoic acid (9)

Method A. (Diacetoxyiodo)benzene (770 mg, 2.39 mmol) was added to a suspension of 8 (600 mg, 1.09 mmol) and 2,2,6,6-Tetramethyl-1-piperidinyloxy (TEMPO) (43 mg, 0.28 mmol) in 1:1 acetonitrile/water (50 mL), and the resulting mixture was stirred at rt for 48 h, then diluted with water (100 mL) and extracted with dichloromethane (3×150 mL). The combined organic extracts were washed with brine (30 mL), dried over sodium sulfate, filtered and concentrated to a crude that was purified by tlc-grade silica gel flash chromatography. Elution with dichloromethane to 1:49 allowed to recover unreacted 8 (140 mg, 25%); subsequent elution with 1:19 to 2:23 methanol/dichloromethane gave 9 as a yellow solid, containing some impurities (190 mg, 31%). A small amount of pure 9 was obtain by preparative silica gel tlc (3:17 methanol/dichloromethane, washed with 2:23 methanol/dichloromethane) as a white solid. $R_f$ 0.44 (3:17 methanol/dichloromethane); mp 198-200° C. (dec.); $[\alpha]_D^{22}$ −11.43 (c 0.30, $CHCl_3$); UV (MeOH) $\lambda_{max}$ 264.0, 299.0, 288.5; $^1H$ NMR (DMSO-$d_6$, 400 MHz) δ 9.87 (bs, 1H), 8.80 (s, 1H), 8.20 (d, J=8.8, Hz, 1H), 7.89 (d, 2H, J=7.4 Hz), 7.75-7.72 (m, 3H), 7.42 (t, 2H, J=7.4 Hz), 7.34 (d, 2H, J=7.4 Hz), 6.49 (d, J=4.5 Hz, 1H), 5.60 (t, 1H, J=4.9 Hz), 4.55-4.49 (m, 1H), 4.36-4.29 (m, 2H), 4.24-4.16 (m, 2H), 1.96 (s, 3H); $^{13}C$ NMR (DMSO-$d_6$, 100 MHz) δ 173.3, 169.3, 155.9, 151.8, 151.5, 149.1, 146.8, 143.9, 143.8, 140.7, 131.3, 127.7, 127.2, 127.1, 125.4, 125.3, 120.2, 120.1, 86.3, 83.5, 75.7, 65.9, 55.4, 46.6, 20.4; Mass ($[M+H]^+$) 564.

Method B. Ruthenium (III) chloride monohydrate (7.5 mg, 0.04 mmol) was added to a vigorously stirred biphasic heterogeneous mixture of 8 (90 mg, 0.16 mmol) and sodium periodate (145 mg, 0.68 mmol) in water (6 mL), acetonitrile (4 mL) and carbon tetrachloride (4 mL) at rt, and the resulting mixture was stirred at rt for 72 h. Solvents were then evaporated under reduced pressure, the residue was dissolved in methanol, tlc-grade silica gel was added, and the solvent was removed under reduced pressure. The residue was loaded on a very thin pad of tlc-grade silica gel column packed with dichloromethane and eluted with a gradient of dichloromethane to 1:19 methanol/dichloromethane to give 9 as a dark yellow oil (40 mg, 43%). Even though this product looked clean by tlc, repeated attempts to purify it by preparative silica gel tlc did not result in the isolation of a solid.

L-3'-Deoxy-$N^6$-methyl-3'-methylaminoadenosine-5'-methylcarboxamide (2)

Triethylamine was added to a solution of 9 (200 mg, 0.36 mmol) and ethyl chloroformate (40 μL, 0.42 mmol) in anhydrous N,N-dimethylformamide (5 mL) at 0° C., and the resulting mixture was stirred at 0° C. for 10 min, then treated with a 40% methylamine solution in water (5 mL). The mixture was allowed to warm up to rt, then stirred for 48 h. Solvents were evaporated in vacuo and the residue was purified by flash silica gel chromatography (dichloromethane to 1:13 methanol/dichloromethane) to give an orange solid that was further purified by preparative silica gel tlc: $R_f$ 0.20 (3:17 methanol/dichloromethane) to give pure 2 as an off-white solid (60 mg, 55%). $^1H$ NMR (DMSO-$d_6$, 400 MHz) δ 8.34 (s, 1H), 8.30 (bs, 1H), 6.07 (d, J=4.1 Hz, 1H), 4.62 (dd, J=5.3, 4.1 Hz, 1H), 4.34 (d, J=5.7 Hz, 1H), 3.86-3.84 (m, 1H), 3.80 (t, J=5.7 Hz, 1H), 3.11 (bs, 3H), 2.83 (s, 3H); $^{13}C$ NMR (DMSO-$d_6$, 100 MHz) δ 172.9, 156.8, 153.9, 149.0, 121.4, 92.1, 83.6, 74.6, 50.0, 26.3, 25.6; Mass ($[M+H]^+$) 308.

Example 2

Cardioprotective Activity in Langendorff Perfused Mouse Heart

Hearts were isolated from 10 weeks old male Swiss Webster white mice and perfused with Krebs buffer containing (mM): NaCl, 118; $NaHCO_3$, 25; KCl, 4.7; $Mg_2SO_4$, 1.2; $KH_2PO_4$, 1.2; glucose, 11; $CaCl_2$, 1.8, as previously described in detail. Buffer was equilibrated with 95% $O_2$, 5% $CO_2$ at water-jacketed reservoirs maintained at 37° C. After thoracotomy, hearts were excised into ice-cold perfusion buffer, the aorta was cannulated (20 gauge PVC cannula) and perfused at 100 cm $H_2O$ pressure. A fluid filled silicon balloon was inserted into the left ventricle via the mitral valve. The balloon was attached to a pressure transducer connected to a Power Lab data acquisition system for the recording of left ventricular pressure (ADInstruments, Colorado, USA). Hearts were immersed in perfusate at 37° C. and balloons inflated to an end diastolic pressure of ~10 cm $H_2O$. Hearts were stabilized for 20 min and baseline functions like left ventricular developed pressure (LVDP) and heart rate (HR) and coronary flow were measured. Hearts showing baseline values of LVDP lower than 80 cm $H_2O$, spontaneous heart rates lower than 300 BPM and/or coronary flow greater than 5 mL/min were disqualified from the study according to previously published criteria. Hearts were untreated or subject to preconditioning stimuli either with adenosine or with synthetic analogs 1 or 2 for a five minutes of perfusion. After the baseline period, all the untreated and treated hearts underwent 40 min global ischemia followed by 60 min reperfusion. The parameters of LVDP and HR were reassessed after reperfusion.

Triphenyltetrazolium Chloride Staining. Hearts were perfused with 1% triphenyltetrazolium chloride (TTC) immediately after completion of the experiment and incubated for 15 min at 37° C. Then the hearts were weighed and sliced into ~1 mm transverse sections and scanned using Microteck film scanner (Miroteck International Inc, New York, USA). The area of infarcted (unstained) and viable (stained) tissue was measured using Adobe Photoshop image analysis software. The ratio of infarct area to total cross sectional area of the ventricle from each slice was determined (percent infarction).

Statistical analysis. Baseline data and post-ischemic functional recoveries in different experimental groups were analyzed by one-way ANOVA with Bonferroni's Correction. A P value of <0.05 was considered significant. All values are presented as Mean±SEM.

Figure 3A:
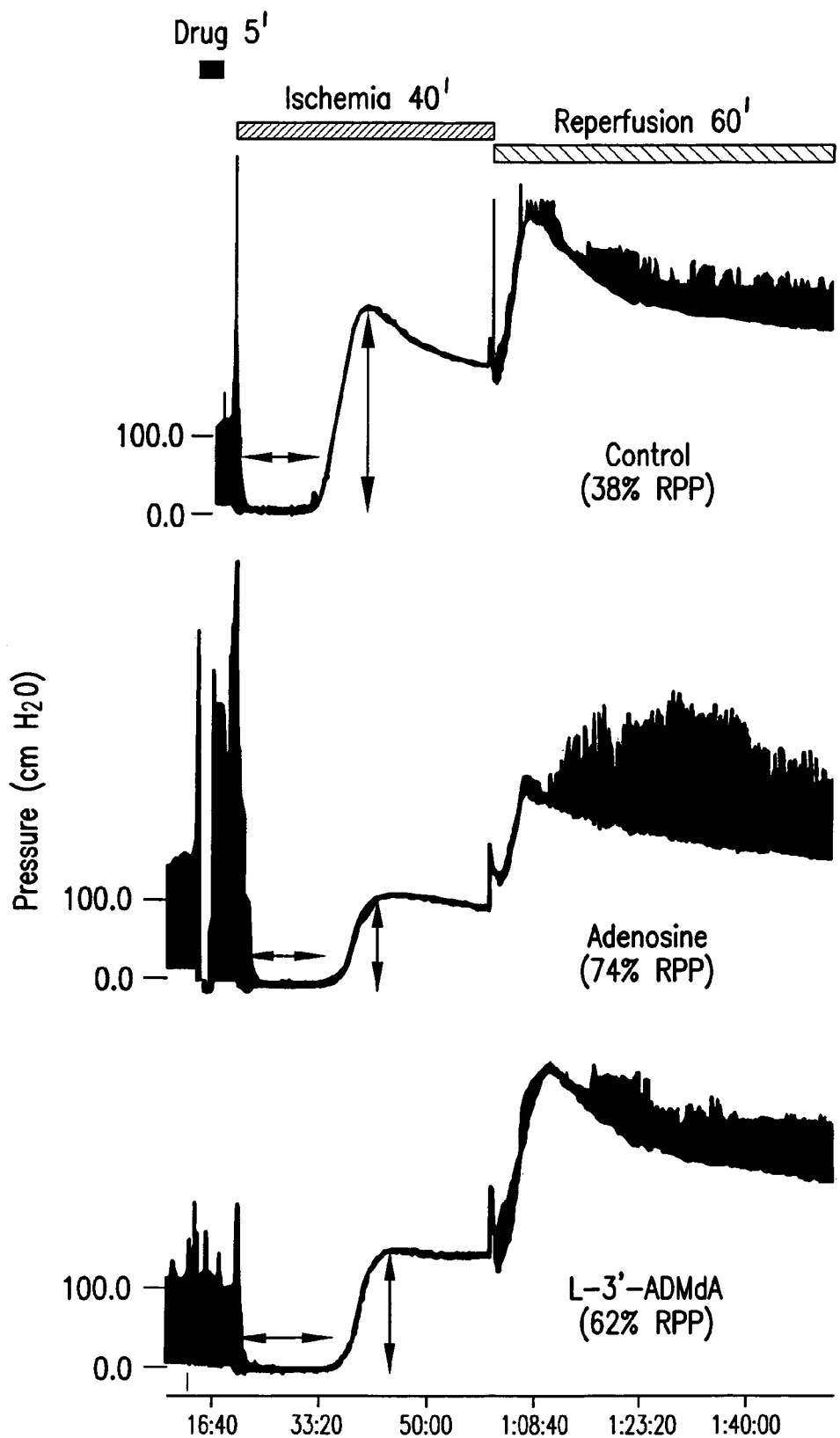
FIG. 3A is a condensed pressure tracings of Langendorff perfused mouse hearts pretreated with adenosine, L-3'-AM-MECA, adenosine or control buffer as indicated. Adenosine (50 μM) produced a transient arrest of contractile activity during its perfusion as previously reported.[15] The percentage recovery of the initial baseline rate-pressure product (RPP) upon reperfusion of these exemplary tracings is indicated. Arrows indicate 'time until contracture' and 'maximal contracture' parameters in each tracing.
Figure 3E:
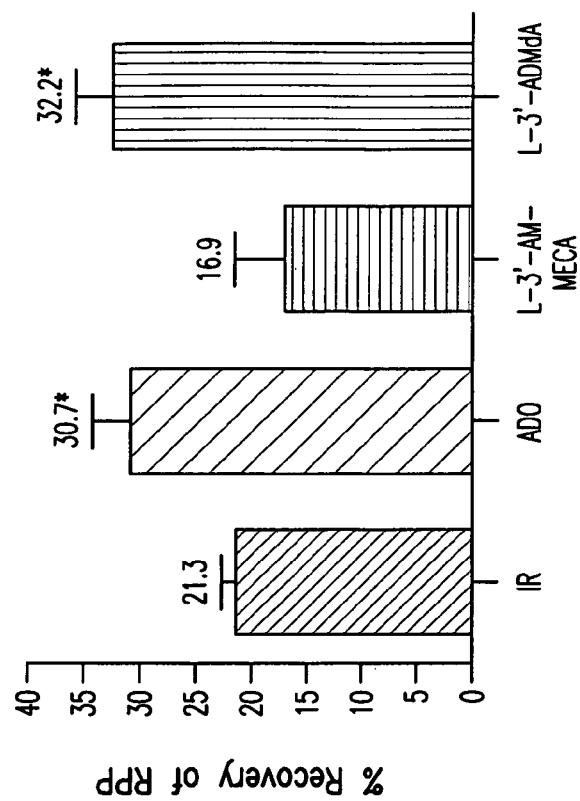
FIG. 3E shows functional recovery of contractility, expressed in % recovery of RPP. * Statistically different from negative control (IR).
Figure 3D:
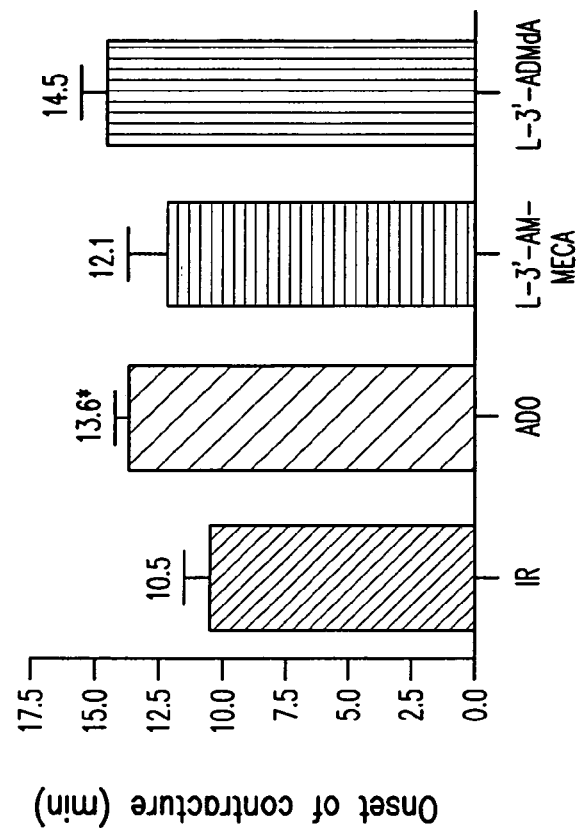
FIG. 3D shows maximum ischemic contracture often correlates to the extent of ischemic ATP depletion and damage.

This example evaluated the cardioprotective effect of (1) and (2) on the well established mouse isolated perfused heart model. The experiments were conducted on Swiss Webster types of mice. In negative controls, hearts were subject to 40 min ischemia, followed by reperfusion. Left ventricular developed pressure (LVDP) was measured before ischemia and, after reperfusion, when the cardiac rhythm stabilized (i.e. absence of arrhythmic contraction). It was determined that the best time was between 50 and 60 minutes from reperfusion. In positive controls, ischemia was preceded by a 5 min treatment with adenosine (during which the known transient cardiac standstill effect was observed) followed by a 2 min washout period. At the end of the experiments, samples of tissue were analyzed by TTC staining techniques to determine the infarction area. This was quantitatively measured by optical methods, which show a protective effect that is comparable or higher than adenosine for both L-PAN (1) and L-3'-AM-MECA (2). FIGS. 3D shows the onset and the extent of the contracture that follows ischemia. This is probably a consequence of ATP depletion, with loss of functionality of $Na^+/K^+$ ATPase, membrane depolarization and influx of $Ca^{++}$. L-PAN (1) displays similar effects as adenosine, increasing the onset of ischemic contracture, whereas (2) does not show a significant effect (FIG. 3D). Both (1) and (2), however, show a significant decrease of maximum ischemic contracture, similarly to adenosine (FIG. 3C). This effect is more significant that the onset time when correlated with ischemic injury. The functional recovery of contractility can be measured by the ratio of the final and initial LVDP corrected by the heart rate according to the following formula:

$$\{(\Delta p_f * rate_f)/(\Delta p_i * rate_i)\} * 100 = \% \text{ RPP}.$$

Alternative protocol: Compounds were perfused for 5 minutes prior to ischemia to evaluate potential protective effects (FIG. 3A). Left ventricular developed pressure (LVDP) was continuously monitored during the ischemia-reperfusion (IR)

protocol and the % functional recovery was expressed as the final rate pressure product (RPP)/initial RPP*100. To assess necrosis after the IR injury, hearts were evaluated by perfusing them with a 1% TTC solution, which stains viable tissue red. High resolution scans were made of transverse sections of heart and the infarction area (i.e., not stained red) was determined and expressed as a % of total tissue area. In addition, images were also red-green-blue split using ImageJ software and the intensity of red staining was quantitatively determined (FIG. 3B). The cardioprotective effects of adenosine were reflected in: significantly less evidence of necrosis as assessed with TTC staining (FIG. 3B); lower maximal, and a delayed time until onset of ischemic contracture (FIGS. 3C, 3D); and most importantly, significantly increased recovery of function upon reperfusion after 40 minutes of ischemia (FIG. 3E).

Both L-3'-PAN (1) and L-3'-AM-MECA (2) showed decrease of cardiac tissue necrosis (FIG. 3B), and both significantly decreased maximum ischemic contracture (FIG. 3C). L-3'-PAN (1) also displayed similar effects as adenosine by increasing the time until onset of ischemic contracture, whereas L-3'-AM-MECA (2) did not significantly alter this parameter (FIG. 3D). Similarly, pretreatment with L-3'-PAN resulted in significant functional recovery of contractility, whereas L-3'-AM-MECA did not show any significant effect (FIG. 3E). These differences may indicate different subtype selectivity profile. Interestingly, unlike adenosine, neither showed cardiac standstill during treatment.

Example 3

AR Agonist Activity in L6 Myoblasts

Figure 4:
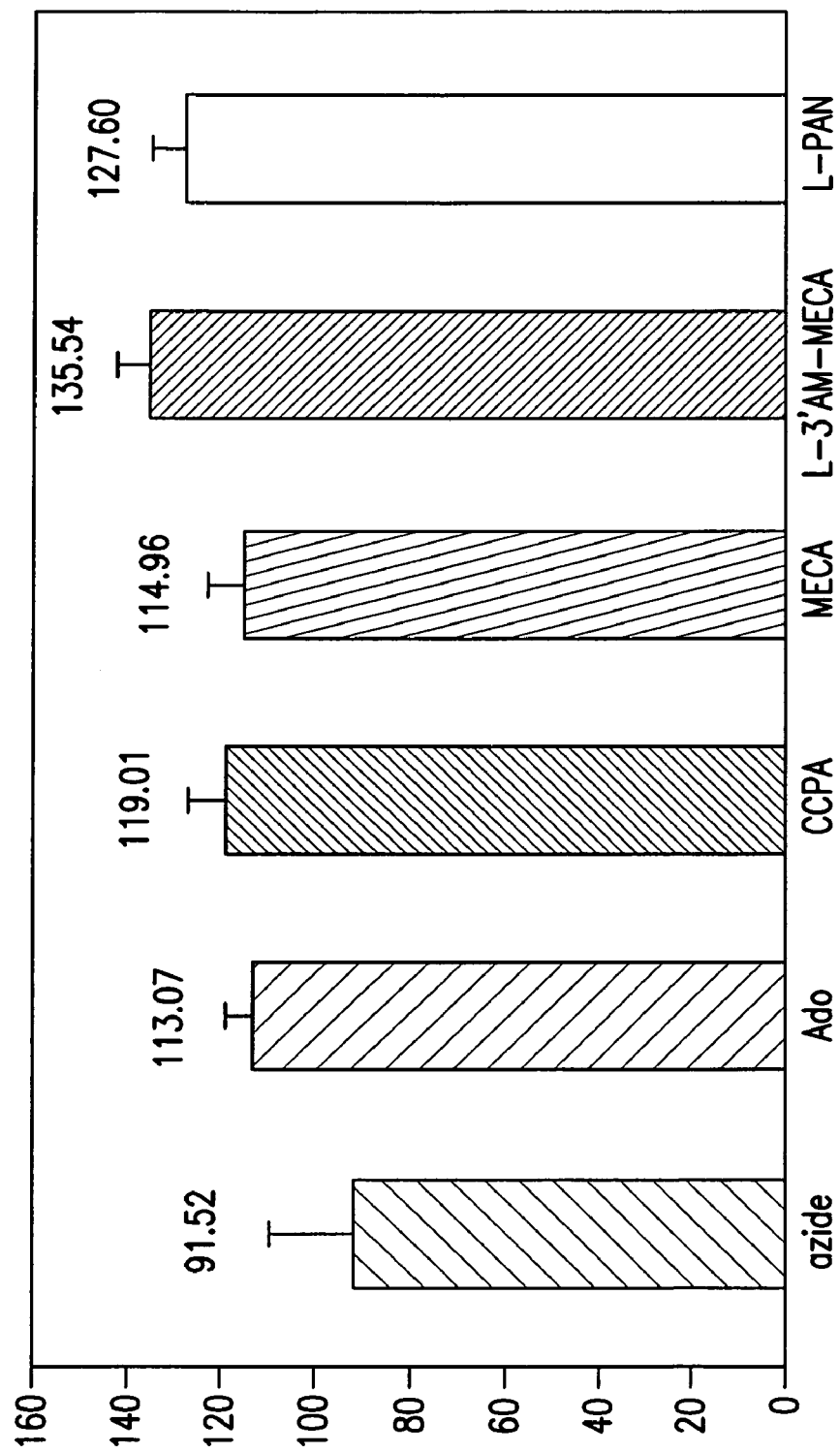
FIG. 4 is a graph showing the effect of L-PAN (1) and L-3'-AM-MECA (2) on the azide-induced Pasteur effect in L6 myoblasts.
Figure 5:
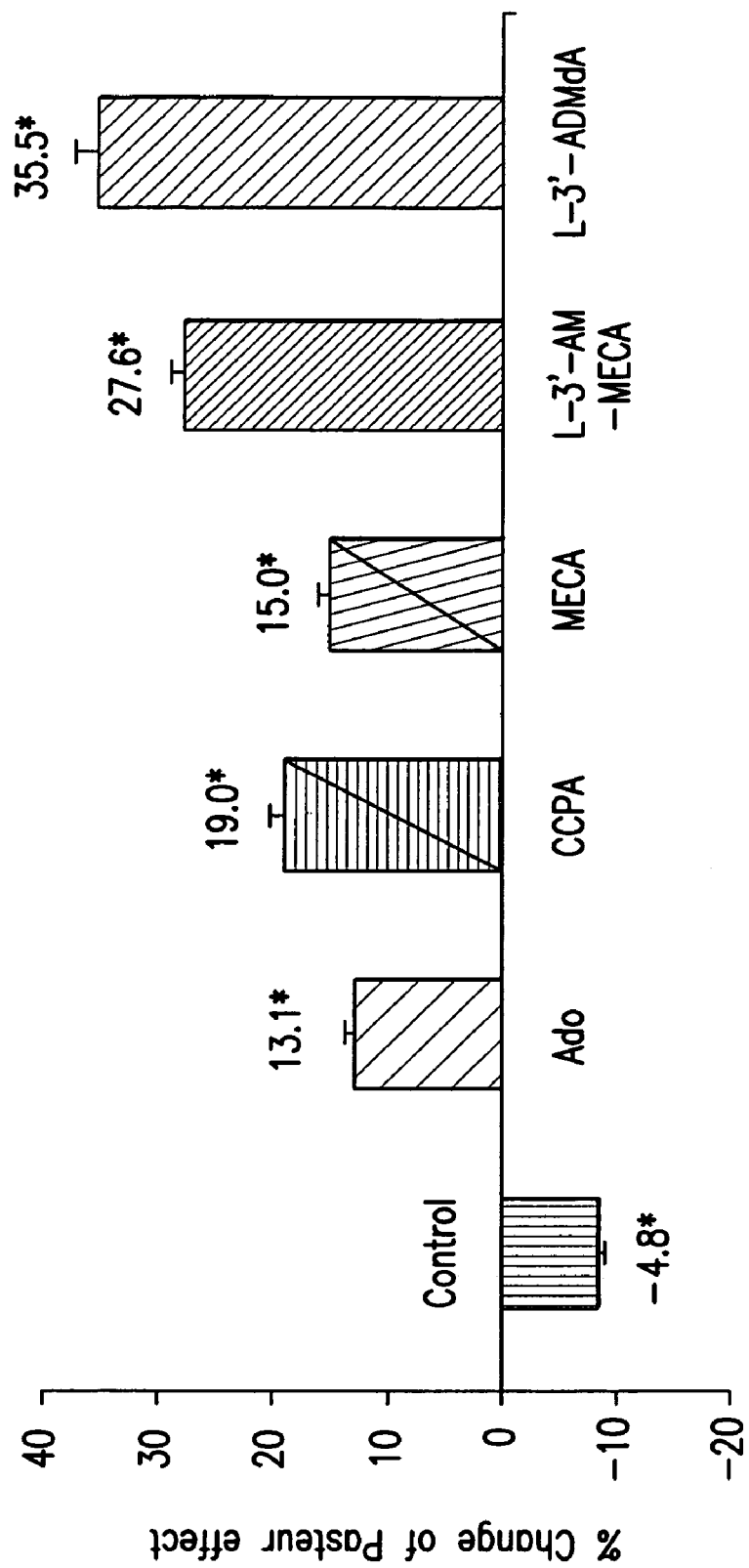
FIG. 5 is a graph showing increase of the azide-induced Pasteur effect on L6 myoblasts by L-3'-AM-MECA (2) and L-3'-ADMdA (1). Percent changes in extracellular acidification rates upon treatment of L6 cells with sodium azide (5 mM) are shown. Responses are the average for 10 min exposure and these are normalized to the increase measured for the first exposure of the same cells to azide 30 min prior. Typically the second exposure causes a diminished Pasteur effect (see control). Error bars are SEM for n=3-5. * Statistically different from negative control (IR).

The ability of increasing the azide-induced Pasteur in L6 myoblasts was measured by microphysiometer. Both (1) and (2) increased the Pasteur effect by 136% and 128% respectively compared to the (13% increase observed with adenosine, (1) 19% for the selective $A_1$ agonist CCPA and 115 for the $A_1/A_3$ agonist MECA (FIG. 4). Because adenosine receptors are involved in the Pasteur effect, this effect, along with the cardioprotection showed above, strongly supports an agonistic effect on adenosine receptors. Currently, we are performing the same microphysiometer assay in the presence of selective antagonists to $A_1$ and $A_3$ selective antagonists. If the selective antagonist to a receptor reverts the observed effect, the considered molecule will be an agonist to that receptor.

Results Summary

The L-adenosine analogs L-3'-amino-3'-deoxy-$N^6$-dimethyladenosine (L-puromycin aminonucleoside, (L-PAN; 1) and L-3'-amino-3'-deoxy-$N^6$-methyladenosine-5'-N-methyluronamide (L-3'-AM-MECA; 2) are agonists to the adenosine receptors. In an ischemia/reperfusion model on Langendorff perfused mouse heart, both (1) and (2) showed cardioprotective action comparable to adenosine, as measured by decreased infarction area (39.8±5.7 and 31.8±5.4% respectively, compared to 58.3±5.8% for the negative control and 24.6±5.8% for adenosine) and decreased maximum ischemic contracture (74.3±7.8 and 87.6±6.3 cmH$_2$O respectively, compared to 105.0±6.8 cmH$_2$O for the negative control and 74.1±15.6 cmH$_2$O for adenosine). L-PAN (1) also showed functional recovery (32.2±3.7 cmH$_2$O/s % rate pressure product, compared to 21.3±1.4 for the negative control and 30.7±3.4 for adenosine) and increased onset of contracture (14.5±0.9 min, compared to 10.5±1.0 min for the negative control and 13.6±0.6 min for adenosine) comparable to adenosine. In contrast, L-3'-AM-MECA (2) did not show significant functional recovery nor increased onset of contracture compared to control. Unlike adenosine, neither (1) nor (2) induce cardiac standstill in mouse heart. In a cell model, both (1) and (2) increased the azide-induced Pasteur effect in L6 mycoblasts by 136% and 128% respectively compared to the 113% increase observed with adenosine. Experiments conducted in the presence of selective $A_1$ and $A_3$ antagonists can be used to determine the subtype selectivity of (1) and (2).

In summary, the molecules disclosed herein are non natural L-enantiomers of modified puarine nucleosides. In the past, L-nucleosides have shown activity as antiviral and as anticancer agents by virtue of their ability to interact with human kinases and inhibit viral or human nucleic acid polymerises. The first L-nucleosides acting as agonists to AR has been described. Since the activity of known antiviral and antitumor L-nucleosides is due to metabolic activation to their triphosphate via interaction with nucleoside kinases, the compounds disclosed herein are the only known examples of L-nucleosides that interact with animal enzymes different than kinases or polymerases. This discovery opens a new niche in the search for AR ligands. The nature of L-nucleosides is likely to endow potential candidates with favorable features such as lower toxicity and higher metabolic stability than their D-counterparts.

As a drug, the disclosed compounds are likely to enjoy the benefits deriving from their nature of being an L-nucleoside, such as low cellular toxicity, metabolic stability and long-lasting action.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

REFERENCE

Nair, V., and Emanuel, D. J., Synthetic design, stereochemistry, and enzymatic activity of a reversed aminoacyl nucleoside: An analogue of puromycin. J. Am. Chem. Soc. 1977, 99, 1571-1576.

Baker, B. R., Schaub, R. E., and Williams, J. H., Puromycin. Synthetic studies. VIII. Synthesis of 3-amino-3-deoxy-D-ribofuranoside derivatives. A second synthesis of 3-amino-3-deoxy-D-ribose. J. Am. Chem. Soc. 1955, 77, 7-12.

Baker, B. R., Schaub, R. E., Joseph, J., and Williams, J. H., Puromycin. Synthetic studies. IX. Total synthesis. J. Am. Chem. Soc. 1955, 77, 12-15.

Wang, M., Zhang, J., Andrei, D., Kuczera, K., Borchardt, R. T., and Wnuk, S. F. Are L-adenosine and its derivatives substrates for S-adenosyl-L-homocysteine hydrolase? J. Med. Chem., 2005, 48, 3649-3653.

1. Fredholm, B. B.; Ijzerman, A. P.; Jacobson, K. A.; Klotz, K.-N.; Linden, J. International Union of Pharmacology. XXV. Nomenclature and classification of adenosine receptors. Pharmacol. Rev. 2001, 53, 527-552.

2. (a) Donato, M.; Gelpi, R. J. Adenosine and cardioprotection during reperfusion—an overview. Mol. Cell. Biochem. 2003, 251, 153-159. (b) de Jonge, R.; de Jong, J. W.; Giacometti, D.; Bradamante, S. Role of adenosine and glycogen in ischemic preconditioning of rat hearts. Eur. J Pharmacol. 2001, 414, 55-62. (c) de Jong, J. W.; de Jonge, R.; Keijzer, E.; Bradamante, S. The role of adenosine in preconditioning. Pharmacol. Ther. 2000, 87, 141-149.

3. (a) Glover, D. K.; Riou, L. M.; Ruiz, M.; Sullivan, G. W.; Linden, J.; Rieger, J. M.; Macdonald, T. L.; Watson, D. D.; Beller, G. A. Reduction of infarct size and post-ischemic inflammation from ATL-146e, a highly selective adenosine $A_{2A}$ receptor agonist, in reperfused canine myocardium. *Am. J. Physiol. Heart Circ. Physiol.* 2005, 288, H1851-H1858. (b) Hein, T. W.; Wang, W.; Zoghi, B.; Muthuchamy, M.; Kuo, L. Functional and molecular characterization of receptor subtypes mediating coronary microvascular dilation to adenosine. *J. Mol. Cell Cardiol.* 2001, 33, 271-282. (c) Jordan, J. E.; Zhao, Z. Q.; Sato, H.; Taft, S.; Vinten-Johansen, J. Adenosine $A_2$ receptor activation attenuates reperfusion injury by inhibiting neutrophils accumulation, superoxide generation, and coronary endothelial adherence. *J. Pharmacol. Exp. Ther.* 1997, 280, 301-309.

4. Müller, C. E. Medicinal chemistry of adenosine $A_3$ receptor ligands. *Curr. Top. Med. Chem.* 2003, 3, 445-462.

5. (a) DeNinno, M. P.; Masamune, H.; Chenard, L. K.; DiRico, K. J.; Eller, C.; Etienne, J. B.; Tickner, J. E.; Kennedy, S. P.; Knight, D. R.; Kong, J.; Oleynek, J. J.; Tracey, W. R.; Hill, R. J. 3'-Aminoadenosine-5'-uronamides: discovery of the first highly selective agonist at the human adenosine $A_3$ receptor. *J. Med. Chem.* 2003, 46, 353-355. (b) Tracey, W. R.; Magee, W. P.; Oleynek, J. J.; Hill, R. J.; Smith, A. H.; Flynn, D. M.; Knight, D. R. Novel $N^6$-substituted adenosine 5'-N-methyluronamides with high selectivity for human adenosine $A_3$ receptors reduce ischemic myocardial injury. *Am. J. Physiol. Heart Circ. Physiol.* 2003, 285, H2780-H2787. (c) Tracey, W. R.; Magee, W.; Masamune, H.; Kennedy, S. P.; Knight, D. R.; Buchholz, R. A.; Hill, R. J. Selective $A_3$ receptor stimulation reduces ischemic myocardial injury in the rabbit heart. *Cardiovasc. Res.* 1997, 33, 410-415.

6. Angulo, E.; Casadó, V.; Mallol, J.; Canela, E. I.; Viñals, F.; Ferrer, I.; Lluis, C.; Franco, R. $A_1$ Adenosine receptors accumulate in neurodegenerative structures in Alzheimer's disease and mediate both amyloid precursor protein processing and tau phosphorylation and translocation. *Brain Pathol.* 2003, 13, 440-451.

7. Dall'Igna, O. P.; Porciúncula, L. O.; Souza, D. O.; Cunha, R. A.; Lara, D. R. Neuroprotection by caffeine and adenosine $A_{2A}$ receptor blockade of β-amyloid neurotoxicity. *Brit. J. Pharmacol.* 2003, 138, 1207-1209.

8. (a) Pinna, A.; Volpini, R.; Cristalli, G.; Morelli, M. New adenosine $A_{2A}$ receptor antagonists: actions on Parkinson's disease models. *Eur. J Pharmacol.* 2005, 512, 157-164. (b) Vu, C. B.; Pan, D.; Peng, B.; Kumaravel, G.; Smits, G.; Jin, X.; Phadke, D.; Engber, T.; Huang, C.; Reilly, J.; Tam, S.; Grant, D.; Hetu, G.; Petter, R. C. Novel diamino derivatives of [1,2,4]triazolo[1,5-a][1,3,5]triazine as potent and selective adenosine $A_{2a}$ receptor antagonists. *J. Med. Chem.* 2005, 48, 2009-2018. (c) Vu, C. B.; Peng, B.; Kumaravel, G.; Smits, G.; Jin, X.; Phadke, D.; Engber, T.; Huang, C.; Reilly, J.; Tam, S.; Grant, D.; Hetu, G.; Chen, L.; Zhang, J.; Petter, R. C. Piperazine derivatives of [1,2,4]triazolo[1,5-a][1,3,5]triazine as potent and selective adenosine $A_{2a}$ receptor antagonists. *J. Med. Chem.* 2004, 47, 4291-4299. (d) Dall'Igna, O. P.; Souza, D. O.; Lara, D. R. Caffeine as a neuroprotective adenosine receptor antagonist. *Ann. Pharmacother.* 2004, 38, 717-718. (d) Chase, T. N.; Bibbiani, F.; Bara-Jimenez, W.; Dimitrova, T.; Oh-Lee, J. D. Translating $A_{2a}$ antagonist KW6002 from animal models to parkinsonian patients. *Neurology* 2003, 61, S107-S111. (e) Schwarzschild, M. A.; Xu, K.; Oztas, E.; Petzer, J. P.; Castagnoli, K.; Castagnoli Jr., N.; Chen, J.-F. Neuroprotection by caffeine and more specific $A_{2a}$ receptor antagonists in animal models of Parkinson's disease. *Neurology* 2003, 61, S55-S61. (f) Chen, J. F.; Xu, K.; Petzer, J. P.; Staal, R.; Xu, Y. H.; Beilstein, M.; Sonsalla, P. K.; Castagnoli, K.; Castagnoli Jr., N.; Schwarzschild, M. A. Neuroprotection by caffeine and $A_{2A}$ adenosine receptor inactivation in a model of Parkinson's disease. *J. Neurosci.* 2001, 21, 143-148.

9. Behan, W. M. H.; Stone, T. W. Enhanced neuronal damage by co-administration of quinolinic acid and free radicals, and protection by adenosine $A_{2a}$ receptor antagonists. *Brit. J. Pharmacol.* 2002, 135, 1435-1442.

10. Okainura, T.; Kurogi, Y.; Hashimoto, K.; Sato, S.; Nishikawa, H.; Kiryu, K.; Nagao, Y. Structure-activity relationships of adenosine $A_3$ receptor ligands: new potential therapy for the treatment of glaucoma. *Bioorg. Med. Chem. Lett.* 2004, 14, 3775-3779.

11. Blum, D.; Gall, D.; Galas, M.-C.; d'Alcantara, P.; Bantubungi, K.; Schiffmann, S. N. The adenosine $A_1$ receptor agonist adenosine amine congener exerts a neuroprotective effect against the development of striatal lesions and motor impairments in the 3-nitropropionic acid model of neurotoxicity. *J. Neurosci.* 2002, 22, 9122-9133.

12. (a) Fishman, P.; Bar-Yehuda, S.; Madi, L.; Cohn, I. A3 adenosine receptor as a target for cancer therapy. *Anticancer Drugs* 2002, 13, 437-443. (b) Fishman, P.; Bar-Yehuda, S.; Barer, F.; Madi, L.; Multani, A. S.; Pathak, S. The A3 adenosine receptor as a new target for cancer therapy and chemoprotection. *Exp. Cell Res.* 2001, 269, 230-236.

13. (a) Mustafa, S. J.; Askar, A. 0. Evidence suggesting an $R_a$-type adenosine receptor in bovine coronary arteries. *J Pharmacol. Exp. Ther.* 1985, 232, 49-56. (b) Burnstock, G.; Hills, J. M.; Hoyle, C. H. Evidence that the P1-purinoceptor in the guinea-pig taenia coli is an A2-subtype. *Br. J. Pharmacol.* 1984, 81, 533-541. (c) Brown, C.; Burnstock, G.; Cusack, N. J.; Meghji, P.; Moody, C. J. Evidence for stereospecificity of the P1-purinoceptor. *Br. J. Pharmacol.* 1982, 75, 101-107. (d) Cusack, N. J.; Planker, M. Relaxation of isolated taenia coli of guinea-pig by enantiomers of 2-azido analogues of adenosine and adenine nucleotides. *Br. J Pharmacol.* 1979, 67, 153-158. (e) Cusack, N. J.; Jickman, M. E.; Born, G. V. Effects of D- and L-enantiomers of adenosine, AMP and ADP and their 2-chloro- and 2-azido-analogues on human platelets. *Proc. R. Soc. Lond. B Bio. Sci.* 1979, 206, 139-144.

14. Wang, M.; Zhang, J.; Andrei, D.; Kuczera, K.; Borchardt, R. T.; Wnuk, S. F. Are L-adenosine and its derivatives substrates for S-adenosyl-L-homocysteine hydrolase? *J. Med. Chem.* 2005, 48, 3649-3653.

15. (a) Al Safaijalani, O. N.; Naguib, F. N. M.; el Kouni, M. H. Uptake of nitrobenzylthioinosine and purine β-L-nucleosides by intracellular *Toxoplasma gondii*. *Antimicrob. Agents Chemother.* 2003, 47, 3247-3251. (b) Carter, N. S.; Mamoun, C. B.; Liu, W.; Silva, E. O.; Landfear, S. M.; Goldberg, D. E.; Ullman, B. Isolation and functional characterization of the PfNTI nucleoside transporter gene from *Plasmodium falciparum*. *J. Biol. Chem.* 2000, 275, 10683-10691.

16. (a) Gumina, G.; Chong, Y.; Choo, H.; Song, G.-Y.; Chu, C. K. L-Nucleosides: Antiviral activity and molecular mechanism. *Curr. Top. Med. Chem.* 2002, 2, 1065-1086. (b) Gumina, G.; Song, G.-Y.; Chu, C. K. L-Nucleosides as chemotherapeutic agents. *FEMS Microbiol. Lett.* 2001, 202, 9-15.

17. Jurovcik, M.; Holy, A.; Sorm. F. The utilization of L-adenosine by mammalian tissues. *FEBS Lett.* 1971, 18, 274-276.

18. Gilbert, C. L. K.; Lisek, C. R.; White, R. L.; Gumina, G. Synthesis of L,L-puromycin. *Tetrahedron* 2005, 61, 8339-8344.

19. (a) Tikh, E. I.; Fenton, R. A.; Dobson Jr., J. G. Contractile effects of adenosine A1 and A2A receptors in the isolated murine heart. *Am. J Physiol. Heart Circ. Physiol.* 2005, (b) Peart, J.; Headrick, J. P. Adenosine-mediated early preconditioning in mouse: protective signaling and concentration dependent effects. *Cardiovasc. Res.* 2003, 58, 589-601. (c) Sutherland, F. J.; Baker, K. E.; Shattock, M. J.; Hearse, D. J. Mouse isolated perfused heart: characteristics and cautions. *Clin. Exp. Pharmacol. Physiol.* 2003, 30, 867-878. (d) Sutherland, F. J.; Baker, K. E.; Shattock, M. J.; Hearse, D. J. Responses to ischemia and reperfusion in the mouse isolated perfused heart and the phenomenon of 'contractile cycling'. *Clin. Exp. Pharmacol. Physiol.* 2003, 30, 879-884.

20. (a) Canyon, S. J.; Dobson, G. P. Pretreatment with an adenosine A1 receptor agonist and lidocaine: A possible alternative to myocardial ischemic preconditioning. *J. Thorac. Cardiovasc. Surg.* 2005, 130, 371-377. (b) Nussbaum, E. S.; Sebring, L. A.; Ostanny, I.; Nelson, W. B. Transient cardiac standstill induced by adenosine in the management of intraoperative aneurysmal rupture: Technical case report. *Neurosurgery* 2000, 47, 240-243. (c) De Giovanni, J. V.; Edgar, R. A.; Cranston, A. Adenosine induced transient cardiac standstill in catheter interventional procedures for congenital heart disease. *Heart* 1998, 80, 330-333. (d) Shryock, J. C.; Belardinelli, L. Adenosine and adenosine receptors in the cardiovascular system: biochemistry, physiology, and pharmacology. *Am. J Cardiol.* 1997, 79, 2-10.

21. (a) Patel, H.; Porter, R. H. P.; Palmer, A. M.; Croucher, M. J. Comparison of human recombinant adenosine A2B receptor function assessed by Fluo-3-AM fluorometry and microphysiometry. *Br. J Pharmacol.* 2003, 138, 671-677. (b) Okada, Y.; Taniguchi, T.; Akagi, Y.; Muramatsu, I. Two-phase response of acid extrusion triggered by purinoceptor in Chinese hamster ovary cells. *Eur. J. Pharmacol.* 2002, 455, 19-25. (c) Hafner, F. Cytosensor® Microphysiometer: technology and recent applications. Biosens. *Bioelectron.* 2000, 15, 149-158. (d) Rabinowitz, J. D.; Vacchino, J. F.; Beeson, C.; McConnell, H. M. Potentiometric measurement of intracellular redox activity. *J. Am. Chem. Soc.* 1998, 120, 2464-2473. (d) McConnell, H. M.; Owicki, J. C.; Parce, J. W.; Miller, D. L.; Baxter, G. T.; Wada, H. G.; Pitchford, S. The cytosensor microphysiometer: biological applications of silicon technology. *Science* 1992, 257, 1906-1907.

22. (a) Sutherland, F. J.; Baker, K. E.; Shattock, M. J.; Hearse, D. J. Mouse isolated perfused heart: characteristics and cautions. *Clin. Exp. Pharmacol. Physiol.* 2003, 30, 867-878. (b) Sutherland, F. J.; Baker, K. E.; Shattock, M. J.; Hearse, D. J. Responses to ischemia and reperfusion in the mouse isolated perfused heart and the phenomenon of 'contractile cycling'. *Clin. Exp. Pharmacol. Physiol.* 2003, 30, 879-884.

What is claimed is:

1. A pharmaceutical composition comprising a compound having Formula-I:

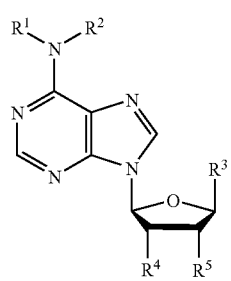

(I)

wherein $R^1$ is methyl, $R^2$ is H, $R^3$ is C(=O)NHCH$_3$, $R^4$ is OH, and $R^5$ is NH$_2$, and a pharmaceutically acceptable carrier.

2. A method of treating a subject with an injury caused by ischemia, comprising administering to the subject an effective amount of one or more of the following compounds:

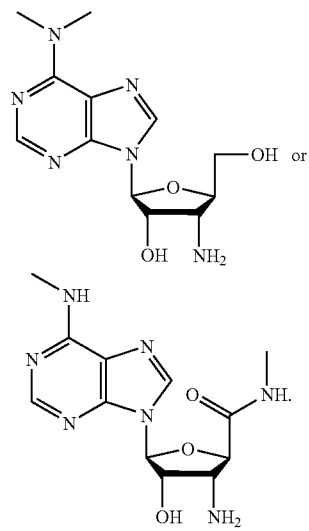

3. A method of inhibiting an AR receptor, comprising contacting the AR receptor with one or more of the following compounds:

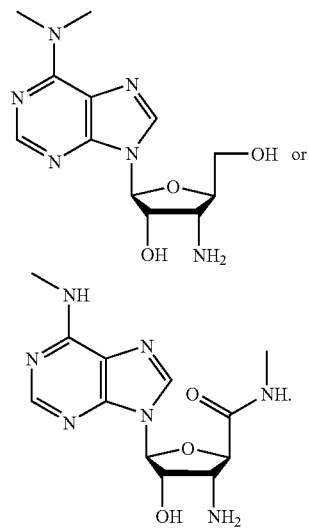

* * * * *